(12) United States Patent
Tessitore

(10) Patent No.: US 12,322,297 B2
(45) Date of Patent: Jun. 3, 2025

(54) ORIENTATION AID SYSTEM FOR BLIND PEOPLE

(71) Applicant: TESMAN RD S.R.L.S, Vescia (IT)

(72) Inventor: Alessandro Tessitore, Monreale (IT)

(73) Assignee: TESMAN RD S.R.L.S., Rome (IT)

( * ) Notice: Subject to any disclaimer, the term of this patent is extended or adjusted under 35 U.S.C. 154(b) by 103 days.

(21) Appl. No.: 17/613,984

(22) PCT Filed: Jun. 5, 2020

(86) PCT No.: PCT/IB2020/055318
§ 371 (c)(1),
(2) Date: Nov. 24, 2021

(87) PCT Pub. No.: WO2020/245791
PCT Pub. Date: Dec. 10, 2020

(65) Prior Publication Data
US 2022/0223069 A1    Jul. 14, 2022

(30) Foreign Application Priority Data

Jun. 5, 2019 (IT) .................. 102019000008178

(51) Int. Cl.
*G09B 21/00* (2006.01)
*H04W 4/80* (2018.01)

(52) U.S. Cl.
CPC ......... *G09B 21/006* (2013.01); *G09B 21/007* (2013.01); *H04W 4/80* (2018.02)

(58) Field of Classification Search
CPC ..... G09B 21/006; G09B 21/007; H04W 4/80; G16H 20/30; G16H 20/40; G16H 40/63; A61F 9/08; A61H 3/061

USPC ......................................................... 340/4.1
See application file for complete search history.

(56) References Cited

U.S. PATENT DOCUMENTS

| 10,052,481 | B2* | 8/2018 | McClure | A61N 1/3787 |
| 2014/0137324 | A1* | 5/2014 | Doering | A47D 9/016 |
| | | | | 5/93.1 |
| 2015/0199918 | A1* | 7/2015 | Jagannathan | G06F 3/017 |
| | | | | 340/4.12 |

(Continued)

FOREIGN PATENT DOCUMENTS

| CN | 102150190 | 8/2011 |
| CN | 109077901 | 12/2018 |
| PT | 104120 A | 12/2009 |

OTHER PUBLICATIONS

Claudio Loconsole et al., Home Haptics: Perception, Devices, Control, and Applications Conference paper an IMU and RFID-based Navigation System Providing Vibrotactile Feedback for Visually Impaired People, Jul. 2016, https://link.springer.com/chapter/10.1007/978-3-319-42321-0_33, Abstract, p. 361-365 (Year: 2016).*

(Continued)

*Primary Examiner* — Omar Casillashernandez
(74) *Attorney, Agent, or Firm* — SHUTTLEWORTH & INGERSOLL, PLC; Timothy J. Klima

(57) ABSTRACT

The present invention is part of the aid devices for blind people and in particular for the dedicated orientation systems. In particular, the present system is suitable both as a domestic aid as well as outdoors, advantageously leaving the user's hands free.

12 Claims, 2 Drawing Sheets

(56) References Cited

U.S. PATENT DOCUMENTS

| | | | |
|---|---|---|---|
| 2016/0063893 A1* | 3/2016 | Kanuganti | H04N 21/8545 |
| | | | 348/62 |
| 2017/0142373 A1* | 5/2017 | Black | G06Q 10/087 |
| 2017/0330441 A1* | 11/2017 | Lin | G08B 21/24 |
| 2021/0128394 A1* | 5/2021 | Roman | A61H 3/061 |
| 2023/0192115 A1* | 6/2023 | Ono | B60W 40/08 |
| | | | 340/435 |

OTHER PUBLICATIONS

An IMU and RFID-based Navigation System Providing Vibrotactile Feedback for Visually Impaired People, Jul. 3, 2016 (Jul. 3, 2016), International Conference on Financial Cryptography and Data Security. [Lecture Notes in Computer Science; Lect.notes Computer], Springer,Berlin, Heidelberg, pp. 360-370,XP047354348,ISBN: 978-3-642-17318-9[retrieved on Jul. 3, 2016]p. 360, paragraph 1-p. 369,paragraph 1 abstract.

Eurasian Examination Report dated Oct. 19, 2022 from counterpart Eurasian Patent Application No. 202193217.

Eurasian Decision to Grant dated Oct. 19, 2022 from counterpart Eurasian Patent Application No. 202193217.

International Search Report dated Sep. 11, 2020 from counterpart PCT App No. PCT/IB2020/055318.

Chinese Office Action dated Nov. 12, 2024 from counterpart CN App No. 202080040226.

Madhura GHARAT et al., Audio Guidance System for Blind, International Conference on Electronics, Communication and Aerospace Technology, ICECA 2017.

European Office Action dated Feb. 13, 2025 from counterpart European App No. 20736766.5.

\* cited by examiner

ORIENTATION AID SYSTEM FOR BLIND PEOPLE

FIELD OF THE INVENTION

The present invention is part of the aid devices for blind people and in particular for the dedicated orientation systems.

STATE OF THE ART

As known, one of the greatest inconveniences for a blind or partially sighted person is represented by the difficulty in orientation, both in closed environments but also and above all in open environments.

In general, we can say that blind and partially sighted people develop a "mental mapping" of a familiar space that surrounds them; for an able-bodied individual who during his/her existence loses sight, this map takes shape from memories; for a born blind person, the details that make up the map come from the knowledge of the environment through the touch. This mental representation of the surrounding space is constantly updated and expanded by any new inputs from outside. More specifically, the main issue for a blind person lies in the fact that said mental mapping is not correctly interpretable until, by touch, a known point of reference is identified that allows to refer the mapping itself to the point where he/she is, by defining some sort of "mental north", subsequently the blind person can only go straight and each step corresponds to a real unit of measurement. Upon identifying a subsequent tactile reference point, the subject stops, and once decided which side to go, the mental map returns to reposition itself again, allowing the individual to resume the journey.

To date, systems have been devised to encourage the orientation of blind people who, however, have not achieved great success, in particular, for example, this is the iBeacon system: technology developed by Apple, configured as an indoor positioning system consisting of a transmitter that uses Bluetooth Low Energy Wireless (BLE) to provide localized services for iPhones and IOS devices (or latest generation Android smartphones). In practice, using low-cost Bluetooth transmitters called "beacons", signals are sent to IOS or ANDROID devices, the installed App processes them and responds by carrying out programmed actions, such as accessing the network or sending notifications to the device.

Basically, if an individual owns a device compatible with the iBeacon system and walks by a point where there is a beacon transmitter, the beacon device locks the compatible device and sends information, for example on the position it is installed in. In relation to this information, the functionality of iBeacon takes the form of sending a notification in the form of a written Pop-up (subsequently converted into audio via Voice-over) to the smartphone video, after installing the relevant application.

This function is clearly not very efficient and not at all practical for a blind person who, among other things, has his/her hands occupied with the smartphone, thus finding autonomy of action limited, particularly disadvantageous having to refer to a device (the smartphone) very difficult to manage without visual interaction.

Furthermore, this system is very expensive since it must take into account, for example, the purchase of a smartphone device that supports the BLE protocol, and again the purchase of any licenses to activate the functions of said beacons.

So, in a totally disadvantageous way, both the costs and (above all) the need to have to use the hands to manage a smartphone enormously limit the possibility of using such a system for a blind user.

It is an object of the present invention to describe an orientation aid system for visually impaired people, that is not an encumbrance, in particular, leaving their hands free.

It is a further object of the present invention to describe an orientation aid system for visually impaired people that is simple and quick to use.

It is still an object of the present invention to describe an aid system for visually impaired people, that is economical in the purchase and use.

It is still an object of the present invention to let a blind person be autonomous when getting around at home and away from home.

It is still an object of the present invention to describe an aid system for blind people within the reach of every user and every operator involved.

BRIEF DESCRIPTION OF THE INVENTION

These and further objects will be achieved thanks to the innovative orientation aid system for blind people in which said system comprises at least a first fixed radio device, which acts as a receiver and/or transmitter, positioned in any internal or external location and at least one further mobile radio device, and at least one remote server connected to at least one fixed radio device, said first mobile radio device being supplied to at least one user characterized in that at least one further second fixed radio receiver/transmitter device is included, said first fixed radio device being the master device, said remote server being connected to said master device, said master device being connected to at least said second fixed slave device, said at least one slave device being able to connect with at least said first mobile radio device, said first mobile radio device includes at least two radio modules, for example Bluetooth, and that can be housed in a first wearable accessory; said system comprising at least a second mobile radio device, receiver/transmitter, comprising at least one radio module, said second mobile radio device being housed in a second wearable accessory, said second mobile radio device being adapted to transmit at least one voice message to a user, said first and second devices being adapted to connect to each other, said first mobile radio device being adapted to connect with said second slave device, subsequently said first mobile radio device being adapted to connect with said second mobile radio device providing said second mobile device at least one audio message to communicate, the user finding his/her way around in close/open spaces Said first wearable accessory connecting to said second wearable accessory by means of said radio modules; said first master device comprising at least two radio modules for example Bluetooth and Wi-Fi to connect to at least one or more further slave devices.

Said first wearable accessory being for example a bracelet and said second wearable accessory being for example an earphone. Said first wearable accessory, however, being a necklace, a watch, a belt or other accessory that can be worn comfortably without encumbering the hands.

Said first wearable accessory also including, in one embodiment, a gyroscope. Still said system optionally also comprising a further fixed auxiliary device comprising a radio receiver/transmitter device comprising for example a Bluetooth module and comprising means suitable for sending audible and luminous warnings.

(Note that here we will not deal with the technology known for implementing smart bands or smartwatches etc., we will only deal with the innovative aspects introduced in them or in similar accessories suitable for the purposes of interest for the present invention.)

Furthermore, also the second mobile device comprising at least one loudspeaker and electronics, can be a classic earphone or an earring, or be integrated in a hat or in the temple of a pair of glasses, or equipped with pliers (or pin) to hook it in an area of the user's clothing that is comfortable to be heard (e.g. jacket or shirt lapel). The at least one first master device, for example, is positioned in a close or open space equipped with WI-FI connection to connect to the cloud server, (which contains information on: owners of the master, slave and mobile devices, positioning of the master and slave, identification of the respective masters and slaves also in relation to where they are positioned), the one or more slave devices, for example, are positioned at a distance covered by the radio signal of the master to connect to it and be able to be linked via radio by said first mobile device when the wearer, or the user, is at a given distance from a first slave.

Basically, in public and/or private close and open spaces, such as homes, pharmacies, shops, parks, public transport, bus stops, etc., a master device and related slaves can be positioned to cover at least an area of interest.

Therefore, when the user approaches a first slave, the user will be sent a voice message from the secondary mobile device, the slave will have communicated the desired message via radio to the first mobile device and the first mobile device will have communicated it to the second mobile device.

In an extremely advantageous way, therefore, said system allows the blind user to receive warning messages about obstacles, or warning messages about points of interest.

Further on we will see that in more detail.

In one embodiment, a sound may be emitted to alert the blind person of the connection between the two mobile devices.

This system, in the first activation phase, comprises a series of steps and actions that take place to activate the various parts of the system, said steps may or may not be considered steps of an associated method that describes the operation of the system:

wear the mobile devices one and two by the user;
connection of at least one master device to the remote (cloud) server via radio;
connection of said master device to at least one (or more) further receiver(s) and/or slave device(s) via radio;
connection between a first and a second wearable accessory (e.g. connection between bracelet and earphone) via radio;
registration on the cloud server of both fixed and mobile devices integrated into wearable accessories with the credentials of the owners and their personal data;
configuration and customization of one or more fixed master and/or slave devices as markers, or to indicate a place/situation and/or the like, with data to be sent to at least one wearable device once said device connects to it;

Furthermore, the most characteristic phases of this innovative system are included, such as:

when a first wearable accessory enters the radio, field emitted by a fixed receiver/transmitter (slave), recognition of the primary wearable device by means of the data present on the cloud stored during registration, subsequent connection for example via Bluetooth between the wearable accessory primary and the slave device;
sending data from the cloud to the master fixed device, subsequently to the slave fixed device to which the primary wearable accessory is connected;
decoding of the data by the primary wearable device and sending said data to the secondary wearable device;
representation of the data received on the secondary wearable device by at least audio and/or visual means;
optionally sending said data by the master fixed device to a slave device with the possibility of representing said data in an audio and visual form, for example, on said slave device;
orientation of one or more users (U) in open and/or closed spaces in safety keeping hands free.

It is observed that there is an example of known art, such as the "DOVI" system described in literature, which although appearing at a first glance similar to the present invention, conceptually moves away from it, in fact, the main difference is precisely in the conception of the two systems; DOVI is a real "navigator" as usually understood in the known art, essentially it returns on the tactile display, the only geolocation, step by step, inside a map.

The system described by the present invention, on the other hand, is a step ahead, providing audio information when it arrives within a range of action of the master or slave device (configurable by the user at will); the information given can be for example the name of the device, the distance, the direction and also an architectural barrier alarm near the device, the system is also equipped with a sound sensor which further indicates the position of the device; therefore the present invention, unlike the known system, anticipates any move by the blind person, warning them well before reaching the area equipped with the device.

The present system is much simpler, the number of basic components per system is in fact only two.

The scope of use is much more extensive, in fact the present system is perfectly suitable for indoors and outdoors, instead the known system herein said is suitable substantially effectively only for indoor environments.

In a particularly advantageous way, thanks to the present system, the user's hands are always free, and he/she must wear a single compact non-annoying device, voice messages are received by means of an earphone, which is neither bulky nor invasive.

The known system implies that the user wears both an ankle device and that he/she can consult a Braille palmtop during movement, this being very uncomfortable and limiting for the simplicity of use.

Furthermore, three tags per environment are sufficient for the present system, for the DOVI system mapping tags placed every 1.5 meters are needed, the onerousness of such an installation is well understood.

On the basis of this descriptive picture, the two systems are significantly different, both from a technical and structural point of view as well as from a functional point of view.

In a particularly advantageous way, the "portable" part of this system is made and integrated into a simple accessory or is comfortably pocket-sized, in addition to a practical earphone.

The known system implies that the user wears at least four devices at the same time, it is immediate to deduce how annoying and frustrating this can be for a user as well as objectively difficult to apply to an aid for daily life.

BRIEF DESCRIPTION OF THE FIGURES

These and further advantages obtained thanks to the innovative orientation aid system for blind people described by the present invention will be better clarified and described with reference to the attached figures, which have an explanatory and non-limiting purpose of the contents of the present invention.

DETAILED DESCRIPTION OF THE FIGURES

Figure 1:
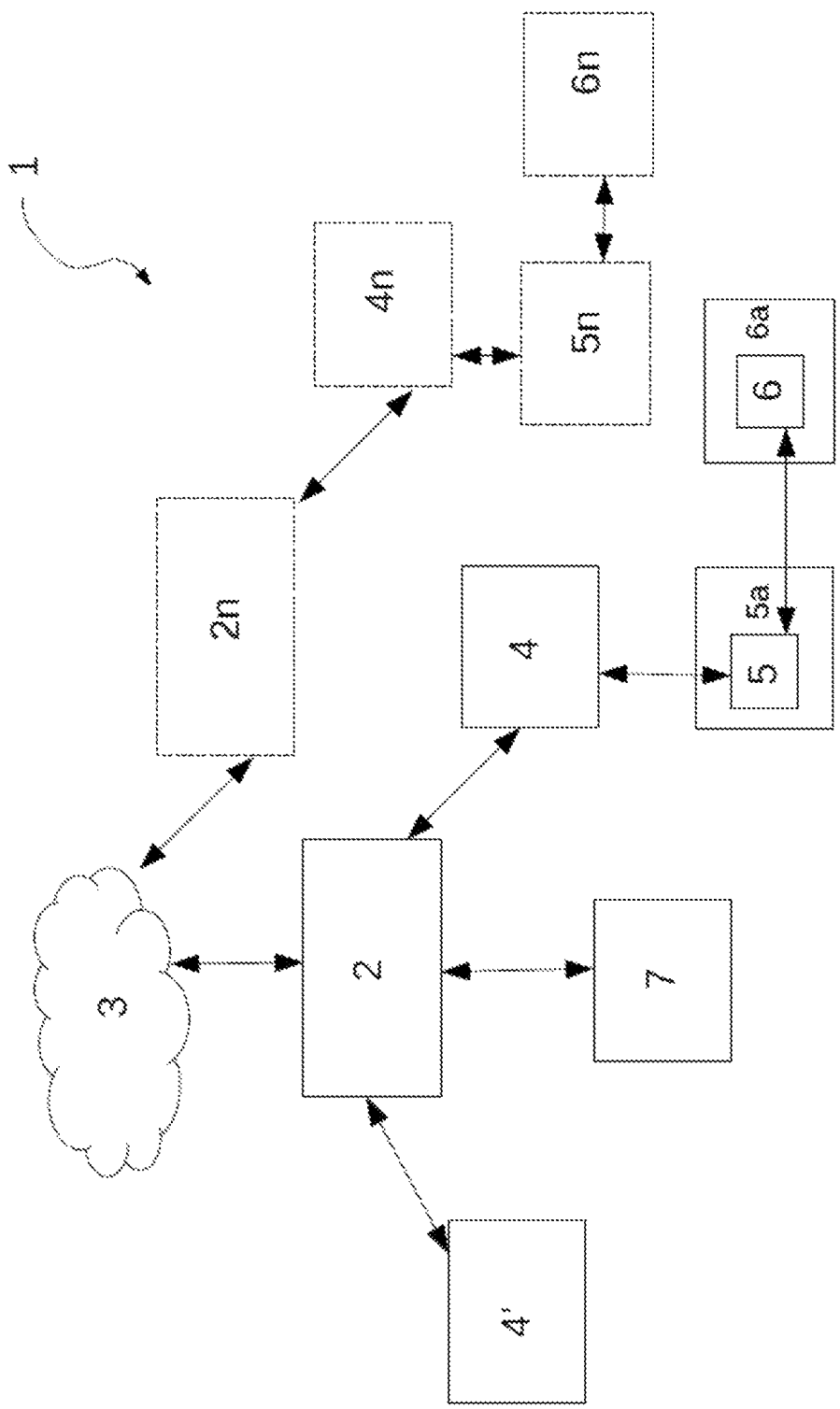
FIG. 1 shows a schematic assembly of the system, in its physical parts and functions.

FIG. 1 shows a graphic example of the architecture of a preferred embodiment of the orientation aid system 1 for blind people in which the master marker 2 is connected via Wi-Fi to a cloud/server 3 and two slave markers 4 and 4', in turn the slave marker 4 is connected for example via Bluetooth to the primary mobile device 5, integrated as already mentioned for example in a bracelet 5a, i.e. wearable accessory, worn on the wrist of a blind user, said bracelet 5a is connected via Bluetooth to a secondary wearable accessory, for example an earphone worn in the ear of a blind user U (not shown here).

The bracelet 5 (for convenience, the primary mobile device/accessory assembly can be summarized) can be connected via radio to marker 4 when it is at a predetermined distance from it, said distance being settable for each marker, for example by acting on the signal strength radio emitted. When paired, the bracelet 5a is then recognized by the cloud server 3.

All information relating to markers 2, 4, 4' and devices/bracelets 5,5a are recorded on the server/cloud 3, in particular the server/cloud 3 which can for example be based on calculation and storage functions, in a first phase of pre-installation of the markers, will be arranged for the registration of the end user by means of a web page, IOS or Android app to give consent to the acquisition of their data in compliance with international directives, insert personal data and further data such as information on the positioning of one or more markers, recording and managing preferably voice messages to be transmitted to the bracelets and anything else that can be programmed or implemented at will. The cloud server will also be able to record information about the owner of one or more bracelets.

Every single Marker 4, 4' . . . 4n after setting and association with a user code generated in the pre-installation phase, each time it performs the pairing with a bracelet 5 i.e. when the bracelet is near the marker 4, it transmits data such as bracelet identification, connection date and time, marker identification. Said cloud or server will therefore verify the existence of said identifiers in the database, and with this information alone, there will be multiple actions that can be performed such as, for example, tracing the owner of the device and locating it.

In addition to this, in a completely innovative and advantageous way, data will be sent from the cloud 3 by means of the master markers 2 . . . 2n and slave 4 . . . 4n to the bracelet 5 . . . 5n which will be converted into audio formats and transmitted to the earphone 6 . . . 6n by bracelet 5 which will inform the blind user by means of an audio message consisting of the information previously entered on the server and relating to that marker 4 to which said bracelet 5 is connected. In particular, still in a completely innovative way, the blind person can for example be informed of being near an obstacle (a step), a danger (a road junction), a commercial activity, tourist information, etc.

In addition, the bracelet 5a being equipped with gyroscopic devices, will be able to provide data on the subject's movements and in particular it will be possible to monitor any states of potential danger to the person, for example by comparing the gyroscopic data for a period of time more or less long. Since these data must be constant over time and transmitted by the same marker, they could indicate the absence of movement and therefore a possible illness. In this case, the cloud/server identifying the general information and the contacts entered relating to the owner can promptly alert, for example, a family member for investigations.

Furthermore, the analysis of the data relating to all the blind owners of the bracelet may suggest improvements to the infrastructures and architectural barriers thanks to an assessment of the preferential movements of these people.

Figure 2:
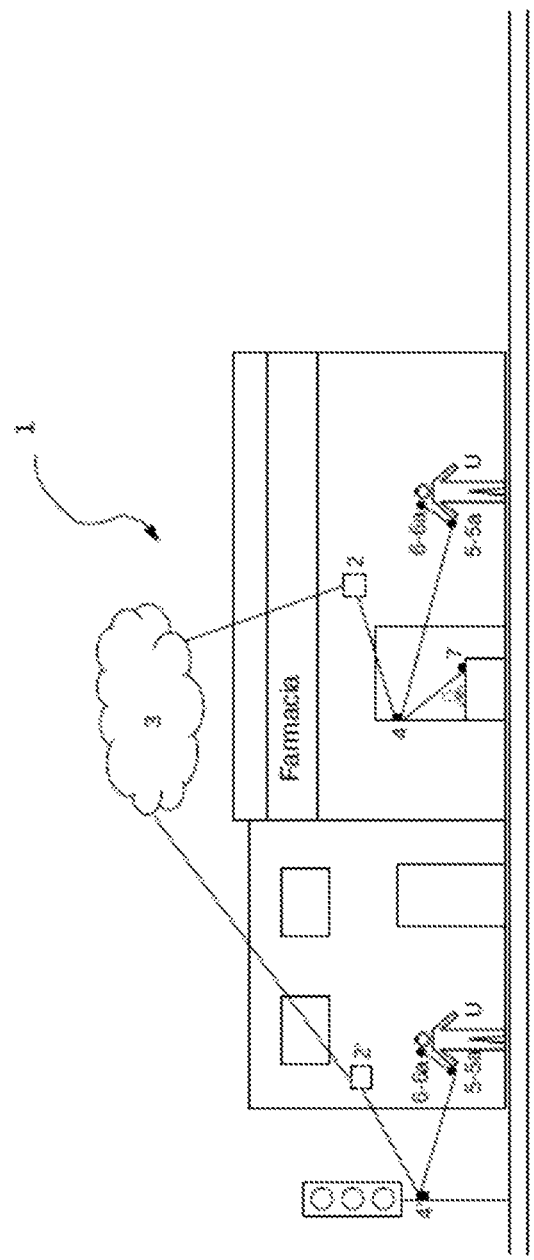
FIG. 2 shows an example of application in an open space.

FIG. 2 shows a typical case of use of the innovative orientation aid system for the blind 1 applied in an external environment.

A user U wearing the bracelet 5a with which the earphone 6a is associated (to be clear: the wearable device 6a is or includes the secondary mobile device 6) approaches the pharmacy where at least one marker (slave) 4 is installed the bracelet enters the range of action of the marker, said bracelet is recognized through a query from the cloud server (through the passage of data between a slave marker, a master marker and the cloud) if the bracelet device is registered on the system, the data is sent from the server characterizing the slave marker with which the connection took place. Said data which will for example be encoded as vocal and which will then pass from the server to the master marker to the slave marker to the bracelet and finally to the earphone, will be audible as an acoustic message to the user; in this case a message could be the simple warning of being in front of a pharmacy, or of paying attention to a step before entering.

In a variant of the system, there may also be a secondary fixed device 7 which can warn the pharmacy staff that a blind person is approaching, alerting the staff employed with acoustic and luminous means. In the same way, said secondary fixed device, with said acoustic means, can invite the blind customer to wait for the arrival of a person in charge to assist him.

Continuing the journey, however, the bracelet 5 of the user U will meet a further slave marker 4' which, as previously described for all data passages, will be able to inform of the presence of an intersection regulated by a traffic light.

It should be noted that, on said primary wearable device 5 or the bracelet, there may be a button for listening to the message received when it has entered the field of action of the slave marker.

With the same operating modes, said system 1 can also be installed inside a home by placing at least one master marker and the various slave markers to warn of a staircase, to orient in a corridor (e.g. "you are in front of the kitchen door") so as to greatly facilitate the orientation of the blind person even in a closed space.

Note that the extreme innovation and the sure advantage lies in the fact that the blind user can be guided only by listening to a voice, without using his/her hands and without having to own a smartphone, since the bracelet is an accessory of minimal impact, as well as little expensive and accessible to most.

In an innovative variant, said orientation aid system for the blind can be represented by the use of a primary wearable device (bracelet x) for normally sighted people. This will be equipped with a display, vibrating sensor and a "free/busy" button.

This X bracelet will be used by normally sighted people, who volunteer themselves to a social service (accompany the blind or follow them during shopping, or other tasks). The task of the bracelet will be, once turned on and placed on the FREE mode, to warn by vibrating when there is a blind person nearby. After vibrating, the display will show the address of the Marker that detected the passage of the person concerned; once the user is reached (equipped with a bracelet), on the bracelet x the "busy" mode can be activated, meaning that from that moment on, the volunteer who wears it is accompanying and offering assistance to the blind person.

All this information, data exchange etc., will be managed and stored on at least one cloud server by means of radio links as already illustrated above.

Finally, a further possibility of development may be represented by the introduction of an additional wearable device on the blind person, for example glasses equipped with a camera, which can also independently recognize a possible solid obstacle placed on the path of the blind person, always communicating with the bracelet and then receive an audio message in the earphone. As already mentioned, these glasses can also be equipped with the second wearable device which will be able to transmit voice messages to the user.

It is evident that the innovative aid system 1 for the visually impaired people is able to solve the aforementioned problems of the known art, therefore it should be noted that variations in materials used for the embodiment of the various devices, their shape, the protocols used for communication between devices, number of various master, slave, primary wearable device, secondary or other wearable devices, codes, data and signal transmission methods, language of messages, etc. they are all variants of the system described and protected by the present invention as better clarified by the appended claims.

The invention claimed is:

1. An orientation aid system for blind people, comprising:
a first fixed radio device receiver/transmitter, positioned in any open or closed space and a first mobile radio device receiver/transmitter, and a remote server connected only to the first fixed radio device, said first mobile radio device being supplied to at least one user,
at least one second fixed radio device receiver/transmitter, said first fixed radio device being a master device and the at least one second fixed radio device being a slave device,
said remote server being connected to only said master device,
said master device being connected to said slave device,
said slave device and said master device both being connectable with said first mobile radio device, said first mobile radio device being adapted to receive from said master device and/or said slave device at least one voice audio message on information about the environment,
said first mobile radio device being adapted to be housed in a first wearable accessory,
a second mobile radio device receiver/transmitter,
said second mobile radio device being housed in a second wearable accessory,
said second mobile radio device being adapted to connect with said first mobile radio device and to receive from said first mobile radio device said at least one voice audio message,
said second mobile radio device being adapted to communicate said at least one voice audio message on information about the environment to said user wearing said second mobile radio device to allow the user to orientate oneself in moving in open/closed spaces in safety,
said first wearable accessory and said second wearable accessory leaving the user's hands always free,
wherein the master device is positioned in an open or closed space equipped with WI-FI connection to connect to said at least one remote server, said at least one remote server comprising at least information about the user, the master device, the slave device, the first mobile radio device, the second mobile radio device, positions of the master device and slave device, identification of the master device and slave device in relation to the respective positions and the first and second mobile radio devices.

2. The orientation aid system for blind people according to claim 1, wherein said first mobile radio device comprises at least two radio modules.

3. The orientation aid system for blind people according to claim 1, wherein said first wearable accessory is a bracelet, a watch, a necklace, or other device suitable for being wearable without encumbering the hands of the user and said second wearable accessory is an earphone, a necklace or other device suitable for being wearable without encumbering the hands of the user.

4. The orientation aid system for blind people according to claim 1, wherein said first wearable accessory also comprises a gyroscope.

5. The orientation aid system for blind people according to claim 1, and further comprising a further fixed auxiliary device comprising a radio receiver/transmitter device and comprising a warning device suitable for sending audible and luminous warnings.

6. The orientation aid system for blind people according to claim 1, wherein said second mobile radio device comprises a loudspeaker and is included in the second wearable accessory.

7. The orientation aid system for blind people according to claim 2, wherein said at least two radio modules include Bluetooth modules.

8. The orientation aid system for blind people according to claim 6, wherein the second wearable accessory is an earphone or an earring, is suitable to be integrated in a hat or in an arm of a pair of glasses, or includes a clamp or pin for affixing to the user's clothing, where it is audible to the user.

9. The orientation aid system for blind people according to claim 1, wherein the at least one slave device is configured to connect to said master device, when said slave device is at a distance covered by the radio signal of the master device, and to be able to be linked via radio by said first mobile device when the user is at a given distance from said slave device to transmit said voice audio message to said first mobile device.

10. The orientation aid system for blind people according to claim 1, wherein said first mobile radio device comprises a button for listening to the voice audio message received when it has entered the field of action of said slave device.

11. A method for implementing an orientation aid system for blind people, comprising:
providing the orientation aid system for blind people, comprising:
a first fixed radio device receiver/transmitter, positioned in any open or closed space and a first mobile radio device receiver/transmitter, and a remote server connected only to the first fixed radio device, said first mobile radio device being supplied to at least one user, at least one second fixed radio device receiver/transmitter, said first fixed radio device being a master device and the at least one second fixed radio device being a slave device, said remote server being connected to only said master device, said master device being connected to said slave device, said slave device and said master device both being connectable with said first mobile radio device, said first mobile radio device being adapted to receive from said master device and/or said slave device at least one voice audio message on information about the environment, said first mobile radio device being adapted to be housed in a first wearable accessory, a second mobile radio device receiver/transmitter, said second mobile radio device being housed in a second wearable accessory, said second mobile radio device being adapted to connect with said first mobile radio device and to receive from said first mobile radio device said at least one voice audio message, said second mobile radio device being adapted to communicate said at least one voice audio message on information about the environment to said user wearing said second mobile radio device to allow the user to orientate oneself in moving in open/closed spaces in safety, said first wearable accessory and said second wearable accessory leaving the user's hands always free, wherein the master device is positioned in an open or closed space equipped with WI-FI connection to connect to said at least one remote server, said at least one remote server comprising at least information about the user, the master device, the follower device, the first mobile radio device, the second mobile radio device, positions of the master device and follower device, identification of the master device and follower device in relation to the respective positions and the first and second mobile radio devices, providing that the user wear the first and second mobile radio devices, connecting the master device to a remote cloud server via radio, connecting the master device to the slave device via radio, connecting between the first wearable accessory and the second wearable accessory via radio, registering on the cloud server of the first and second fixed radio devices, the first and second mobile radio devices combined respectively with the first and second wearable accessories, along with credentials of the user, configuring and personalizing the master device and the slave device as markers, or to signal a place/situation, with data to be sent to at least one chosen from the first and second wearable accessories, recognizing the first wearable accessory by data present in the cloud server, stored during registration, subsequent connection between the first wearable accessory and the slave device when the first wearable accessory enters a radio field emitted by the slave device, sending data from the cloud server to the master device and subsequently to the slave device to which the first wearable accessory is connected;

decoding the data by the first wearable accessory and sending said data to the secondary wearable accessory, representing the data received on the secondary wearable accessory by audibly and/or visually, orienting the user in open and/or closed spaces while keeping the user's hands free.

12. An orientation aid system for blind people, comprising:

a first fixed radio device receiver/transmitter, positioned in any open or closed space and a first mobile radio device receiver/transmitter, and a remote server connected to the first fixed radio device, said first mobile radio device being supplied to at least one user, at least one second fixed radio device receiver/transmitter, said first fixed radio device being a master device and the at least one second fixed radio device being a slave device, said remote server being connected to said master device, said master device being connected to said slave device, said slave device and said master device both being connectable with said first mobile radio device, said first mobile radio device being adapted to be housed in a first wearable accessory, a second mobile radio device receiver/transmitter, said second mobile radio device being housed in a second wearable accessory, said second mobile radio device being adapted to connect with said first mobile radio device, said second mobile radio device being adapted to communicate at least one audio message to said user wearing said second mobile radio device to allow the user to orientate oneself in moving in open/closed spaces in safety, said first wearable accessory and said second wearable accessory leaving the user's hands always free, wherein the master device is positioned in an open or closed space equipped with WI-FI connection to connect to said at least one remote server, said at least one remote server comprising at least information about the user, the master device, the follower device, the first mobile radio device, the second mobile radio device, positions of the master device and follower device, identification of the master device and follower device in relation to the respective positions and the first and second mobile radio devices.

* * * * *

UNITED STATES PATENT AND TRADEMARK OFFICE
CERTIFICATE OF CORRECTION

| | | |
|---|---|---|
| PATENT NO. | : 12,322,297 B2 | Page 1 of 1 |
| APPLICATION NO. | : 17/613984 | |
| DATED | : June 3, 2025 | |
| INVENTOR(S) | : Tessitore | |

It is certified that error appears in the above-identified patent and that said Letters Patent is hereby corrected as shown below:

On the Title Page

Item (73), should read:
TESMAN RD S.R.L.

Signed and Sealed this
Fifth Day of August, 2025

Coke Morgan Stewart
*Acting Director of the United States Patent and Trademark Office*